United States Patent
Connelly et al.

(10) Patent No.: US 10,689,498 B2
(45) Date of Patent: Jun. 23, 2020

(54) CLOSED CELL FOAMS INCLUDING POLY-4-HYDROXYBUTYRATE AND COPOLYMERS THEREOF

(71) Applicant: Tepha, Inc., Lexington, MA (US)

(72) Inventors: Dennis Connelly, Arlington, MA (US); Fabio Felix, Foxborough, NH (US); David P. Martin, Arlington, MA (US); Jon Montcrieff, Foxborough, MA (US); Said Rizk, Windham, NH (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 494 days.

(21) Appl. No.: 14/464,099

(22) Filed: Aug. 20, 2014

(65) Prior Publication Data

US 2015/0057368 A1  Feb. 26, 2015

Related U.S. Application Data

(60) Provisional application No. 61/867,986, filed on Aug. 20, 2013.

(51) Int. Cl.

| | |
|---|---|
| *C08J 9/12* | (2006.01) |
| *A61K 9/12* | (2006.01) |
| *A61K 47/34* | (2017.01) |
| *A61L 15/26* | (2006.01) |
| *A61L 15/42* | (2006.01) |
| *A61L 26/00* | (2006.01) |
| *A61L 27/18* | (2006.01) |
| *A61L 31/06* | (2006.01) |
| *A61L 31/14* | (2006.01) |
| *C08G 63/06* | (2006.01) |
| *C08L 67/04* | (2006.01) |
| *A61L 27/56* | (2006.01) |

(52) U.S. Cl.
CPC .............. *C08J 9/122* (2013.01); *A61K 9/122* (2013.01); *A61K 47/34* (2013.01); *A61L 15/26* (2013.01); *A61L 15/425* (2013.01); *A61L 26/0019* (2013.01); *A61L 26/0085* (2013.01); *A61L 27/18* (2013.01); *A61L 27/56* (2013.01); *A61L 31/06* (2013.01); *A61L 31/146* (2013.01); *C08G 63/06* (2013.01); *C08L 67/04* (2013.01); *C08J 2203/06* (2013.01); *C08J 2203/08* (2013.01); *C08J 2205/052* (2013.01); *C08J 2207/10* (2013.01); *C08J 2367/04* (2013.01); *C08L 2203/02* (2013.01); *C08L 2203/14* (2013.01); *C08L 2205/02* (2013.01)

(58) Field of Classification Search
CPC ......... A61K 47/34; A61K 9/122; A61L 15/26; A61L 15/425; A61L 26/0019; A61L 26/0085; A61L 27/18; A61L 27/56; A61L 31/06; A61L 31/146; C08G 63/06; C08J 9/122; C08L 67/04
See application file for complete search history.

(56) References Cited

U.S. PATENT DOCUMENTS

| | | |
|---|---|---|
| 5,134,171 A | 7/1992 | Hammel |
| 5,210,108 A | 5/1993 | Spinu |
| 5,516,565 A | 5/1996 | Matsumoto |
| 5,811,272 A | 9/1998 | Snell |
| 6,245,537 B1 | 6/2001 | Williams |
| 6,316,262 B1 | 11/2001 | Huisman |
| 6,323,010 B1 | 11/2001 | Skraly |
| 6,548,569 B1 | 4/2003 | Williams |
| 6,555,123 B2 | 4/2003 | Williams |
| 6,585,994 B2 | 7/2003 | Williams |
| 6,610,764 B1 | 8/2003 | Martin |
| 6,623,748 B2 | 9/2003 | Clokie |
| 6,828,357 B1 | 12/2004 | Martin |
| 6,838,493 B2 | 1/2005 | Williams |
| 6,867,247 B2 | 3/2005 | Williams |
| 6,867,248 B1 | 3/2005 | Martin |
| 6,878,758 B2 | 4/2005 | Signer |
| 6,905,987 B2 | 6/2005 | Noda |
| 7,025,980 B1 | 4/2006 | Williams |
| 7,179,883 B2 | 2/2007 | Williams |
| 7,244,442 B2 | 7/2007 | Williams |
| 7,268,205 B2 | 9/2007 | Williams |
| 7,553,923 B2 | 6/2009 | Williams |
| 7,618,448 B2 | 11/2009 | Schmitz |
| 7,641,825 B2 | 1/2010 | Rizk |

(Continued)

FOREIGN PATENT DOCUMENTS

| | | | |
|---|---|---|---|
| DE | 102008018964 | | 3/2009 |
| EP | 2 060 605 | * | 5/2009 |

(Continued)

OTHER PUBLICATIONS

Hori, et al., "Chemical synthesis of high molecular weight poly(3-hydroxybutyrate-co-4-hydroxybutyrate)", Polymer 36:4703-5 (1995).

(Continued)

*Primary Examiner* — Matthew P Coughlin
*Assistant Examiner* — Thurman Wheeler
(74) *Attorney, Agent, or Firm* — Pabst Patent Group LLP

(57) ABSTRACT

Methods to produce substantially closed cell foams with densities less than 0.75 g/cm³, and more preferably less than 0.5 g/cm³, without substantial loss of the polymer's weight average molecular weight, have been developed. The closed cells foams have an open cell content of generally less than 50%, and more preferably an open cell content of less than 20%, and the cells have a maximum diameter of less than 5 mm. The foam may include poly-4-hydroxybutyrate or a copolymer thereof. Preferably, the foam is derived by heating a foam polymer formula to a temperature above the melt temperature of the polymer to form a melt polymer system, adding a blowing agent to produce a foamable melt, extruding the foamable melt through a die to a lower pressure to cause foaming, cooling of the foam, and solidification of the foam. These foam structures can be used for fabrication of medical products.

13 Claims, No Drawings

(56) References Cited

U.S. PATENT DOCUMENTS

| | | |
|---|---|---|
| 8,016,883 B2 | 9/2011 | Coleman |
| 8,034,270 B2 | 10/2011 | Martin |
| 8,039,237 B2 | 10/2011 | Martin |
| 8,231,889 B2 | 7/2012 | Williams |
| 8,287,909 B2 | 10/2012 | Martin |
| 2010/0239834 A1* | 9/2010 | Dietrich ............ C08J 9/0061 428/220 |
| 2011/0306693 A1* | 12/2011 | Bosnyak ............ C08L 67/04 521/91 |
| 2013/0281557 A1* | 10/2013 | Van Horn ............ C08J 9/146 521/97 |

FOREIGN PATENT DOCUMENTS

| | | |
|---|---|---|
| EP | 2060605 | 5/2009 |
| WO | 9520614 | 8/1995 |
| WO | 1999032536 | 7/1999 |
| WO | 200056376 | 9/2000 |
| WO | 2005020825 | 3/2005 |
| WO | 2011119743 | 9/2011 |
| WO | 2011159784 | 12/2011 |
| WO | 2012064526 | 5/2012 |

OTHER PUBLICATIONS

Houk, et al., "Why delta-valerolactone polymerizes and gamma-butyrolactone does not", J. Org. Chem., 73 (7), 2674-8 (2008).
Martin, et al., "Medical Applications of Poly-4-hydroxybutyrate: A Strong Flexible Absorbable Biomaterial", Biochem, Eng. J. 16:97-105 (2003).
Steinbuchel, et al., "Diversity of Bacterial Polyhydroxyalkanoic Acids", FEMS Microbial. Lett. 128:219-28 (1995).
Williams, et al., "Applications of PHAs in Medicine and Pharmacy, in Biopolymers", Polyesters, III, 4:91-127 (2002).

* cited by examiner

CLOSED CELL FOAMS INCLUDING POLY-4-HYDROXYBUTYRATE AND COPOLYMERS THEREOF

CROSS-REFERENCE TO RELATED APPLICATIONS

This application claims the benefit of priority to U.S. Ser. No. 61/867,986, filed on Aug. 20, 2013, the disclosure of which is incorporated herein by reference.

FIELD OF THE INVENTION

The present invention generally relates to closed cell foam structures that have been formed by melt-foaming of compositions including poly-4-hydroxybutyrate (P4HB) and copolymers thereof for use in medical products for both topical and implantable applications.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, Tepha-FLEX® biomaterial) is a strong, pliable thermoplastic polyester that, despite its biosynthetic route, has a relatively simple structure. Upon implantation, P4HB hydrolyzes to its monomer, and the monomer is metabolized via the Krebs cycle to carbon dioxide and water.

The polymer belongs to a larger class of materials called polyhydroxyalkanoates that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production.

Chemical synthesis of P4HB has been attempted, but it has been impossible to produce the polymer with a sufficiently high molecular weight that is necessary for most applications (see Hori, Y., et al., *Polymer* 36:4703-4705 (1995) and Houk, K. N., et al., *J. Org. Chem.*, 2008, 73 (7), 2674-2678).

P4HB is a strong but extensible polymer similar to low density polypropylene, and should not be confused with poly-3-hydroxybutyrate, often referred to as "PHB" or "P3HB". Unlike P4HB, PHB is a brittle polymer that has properties resembling polystyrene. For example, PHB has a melting point and glass transition temperature of approximately 80° C. and 1° C., respectively, and an elongation to break of about 3%, whereas P4HB has a melting point of 60° C., a glass transition temperature of approximately −51° C., and elongation to break of around 1,000%. Thus, PHB and P4HB possess substantially different thermal and physical properties.

U.S. Pat. Nos. 6,245,537, 6,623,748, 7,244,442, and 8,231,889 describe methods of making polyhydroxyalkanoates with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of polyhydroxyalkanoates to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of polyhydroxyalkanoate polymers have been disclosed by U.S. Pat. No. 5,811,272 to Snell et al.

Polyhydroxyalkanoates with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al., U.S. Pat. No. 8,034,270 to Martin et al., WO 2011/119743 to Martin et al., U.S. Pat. No. 8,016,883 to Coleman et al., U.S. Pat. No. 8,287,909 to Martin et al., and WO 2011/159784 to Cahil et al. Several patents including U.S. Pat. Nos. 6,555,123, 6,585,994, and 7,025,980 describe the use of polyhydroxyalkanoates in tissue repair and engineering.

WO 00/56376 to Williams et al. discloses open cell P4HB foams produced by thermal phase separation. The foams were produced by solidifying a cast film of P4HB in dioxane at a temperature below the melting point of dioxane, and evaporating the solvent from this solid material at low pressure. WO 05/020825 to Terenghi et al. discloses an alternative particulate leaching method to form P4HB open cell foams. In this method, P4HB was dissolved in dioxane, mixed with salt particles, pressed into a sheet, frozen at −26° C., lyophilized to remove the solvent, and then the particulate was leached from the sample with water to yield an open cell P4HB foam. Both methods yield an open cell architecture, not a closed cell system, and contain residual solvent.

There currently exists a need for surgical structures including closed cell foams with improved performance. These structures can be used, for example, in both soft and hard tissue repair, to heal wounds, control bleeding, protect wound beds, prevent infection, apply pressure to a tissue surface or structure, prevent movement of bodily fluids, absorb fluids, deliver bioactive agents, reinforce tissue structures, separate tissues, and regenerate tissues.

A number of absorbable materials have been used to produce closed cell foams. For example, U.S. Pat. No. 5,134,171 to Hammel et al. discloses closed cell foams produced from polylactic acid, polyglycolic acid, copolymers of lactic and glycolic acids, and these monomers co-polymerized with various hydroxy acids. U.S. Pat. No. 5,210,108 to Spinu et al. discloses closed cell foams prepared from star-shaped absorbable polymers.

Although polymers and copolymers of lactic and glycolic acids are used to produce various medical devices, these materials do not have ideal properties for many procedures and applications. For example, glycolic acid containing polymers are very sensitive to moisture, release very acidic degradation products that can cause inflammatory reactions, and degrade quickly when implanted in the body.

It is an object of the present invention to provide methods to produce substantially closed cell foams including poly-4-hydroxybutyrate and copolymers thereof with an open cell content of generally less than 50%, and more preferably with an open cell content of less than 20%.

It is a further object of the present invention to provide methods to produce substantially closed cell foams including poly-4-hydroxybutyrate and copolymers thereof that have densities of less than 0.75 g/cm$^3$.

It is another object of the present invention to provide methods to produce substantially closed cell foams wherein the maximum diameter of the cells is less than 5 mm.

It is still a further object of the invention to provide formulations for preparing substantially closed cell foams including poly-4-hydroxybutyrate and copolymers thereof that in addition to a blowing agent include one or more of a plasticizer, surfactant, or nucleant.

It is still a further object of the invention to provide continuous processes to produce substantially closed cell foams including poly-4-hydroxybutyrate and copolymers thereof by melt-foaming with an open cell content of generally less than 50%, and processes to form medical devices from these closed cell foams.

It is still yet another object of the invention to provide substantially closed cell foams of poly-4-hydroxybutyrate and copolymers thereof, which are biocompatible and can be used for medical applications, for example, as devices for use in both soft and hard tissue repair, to heal wounds, control bleeding, protect wound beds, prevent infection, apply pressure to a tissue surface or structure, prevent movement of bodily fluids, absorb fluids, deliver bioactive agents, reinforce tissue structures, separate tissues, prevent adhesions, and regenerate tissues, and including wound dressings, tapes, patches, seals, scaffolds, hemostats, pledgets, wound closure devices, compression bandages, orthopedic foams, surgical foams, and orthodontic devices.

It is therefore an object of the invention to provide continuous processes for production of substantially closed cell foams including poly-4-hydroxybutyrate and copolymers thereof, which can be incorporated into or formed into medical products with excellent physical and mechanical properties for medical applications.

SUMMARY OF THE INVENTION

Closed cell forms formed of poly-4-hydroxybutyrate have substantially closed cell structures in contrast to open cell foams produced by thermal phase separation methods or particulate leaching techniques. The closed cell foams can be used in medical products for both topical and implantable applications, such as wound dressings, devices to prevent infection and adhesions, tapes, patches, seals, scaffolds, hemostats, pledgets, wound closure devices, compression bandages, orthopedic foams, surgical foams, and orthodontic devices. The closed cell foams have densities preferably of less than 0.75 g/cm$^3$, and more preferably less than 0.5 g/cm$^3$, and maximum cell sizes of 5 mm.

The closed cell foams may be made by melt-foaming. This process produces foams with microcellular structures wherein usually at least 50% of the cells of the foam are closed, and separated from each other by thin contiguous walls. This closed cell foam structure is physically distinct from open cell foams where the cells of the foam are connected with each other. The interconnectivity of cells in open cell foams allows easy movement of substances between the cells. This movement can be restricted in closed cell foams. Consequently, closed cell foams have very different properties to open cell foams.

A large number of requirements for the melt-foaming polymer and foaming agent must be met in order to produce closed cell foams. These include: (i) an appropriate melt viscosity and melt strength of the polymer during processing for workability, (ii) a solidification rate that allows entrapment of the gas bubbles by the polymer during cooling, (iii) a heat transfer rate that provides enough time for expansion yet is fast enough to prevent collapse of the cells, (iv) a melt viscosity—temperature profile that allows for timely solidification before reaching the minimum cell collapse viscosity, and (v) selection of a blowing agent: with a volatility at the foaming temperature that supports good foam formation; that beneficially plasterizes the polymer without having a negative impact on the solidification point; and where the molecular migration of the blowing agent does not lead to excessive loss of the agent during foaming, a fall in cell pressure below one atmosphere, and the collapse or shriveling of the foam.

Methods to produce substantially closed cell foams with densities less than 0.75 g/cm$^3$, and more preferably less than 0.5 g/cm$^3$, have been developed. The methods allow the closed cell foams to be produced without substantial loss of the polymer's weight average molecular weight. The closed cells foams have an open cell content of generally less than 50%, and more preferably an open cell content of less than 20%, and the cells have a maximum diameter of less than 5 mm. In the preferred embodiment, the foam comprises poly-4-hydroxybutyrate or copolymer thereof. A particularly preferred structure is a substantially closed cell foam, wherein the foam is derived by heating a foam polymer formula including poly-4-hydroxybutyrate or copolymer thereof, in an extruder to a temperature above the melt temperature of the polymer to form a melt polymer system, adding a blowing agent to produce a foamable melt, and extruding the foamable melt through a die to a lower pressure to cause foaming, cooling of the foam, and solidification of the foam. These foam structures can be used for a variety of purposes including fabrication of medical products.

DETAILED DESCRIPTION OF THE INVENTION

Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Bioactive agent" is used herein to refer to therapeutic, prophylactic or diagnostic agents, such as agents that promote healing and the regeneration of host tissue and therapeutic agents that prevent, inhibit or eliminate a disease or disorder.

"Bicomponent" as generally used herein means a structure containing two or more materials.

"Blend" as generally used herein means a physical combination of different polymers, as opposed to a copolymer formed of two or more different monomers.

"Burst strength" as used herein is determined according to ASTM D6797-02 (Standard Test Method for Bursting Strength of Fabrics Constant-Rate-of-Extension (CRE) Ball Burst Test) at ambient conditions using a ball burst fixture with a 1.6 cm circular opening and a 1 cm diameter half-rounded probe.

"Cell" as generally used herein refers to a cavity contained in a foam.

"Closed cell" as used herein means a cell with a membrane surrounding the cavity that is intact and not perforated. The percentage of closed cells may be determined using a gas pycnometer either by the method of ASTM D6226-10 (Standard test method for open cell content of rigid cellular plastics) or ISO 4590:2002 (Rigid cellular plastics—Determination of the volume percentage of open cells and of closed cells.)

"Compression" as generally used herein refers to the process of force on an object, thereby increasing the density of the object.

"Copolymers of poly-4-hydroxybutyrate" as generally used herein means any polymer including 4-hydroxybutyrate with one or more different hydroxy acid units.

"Elastomer" as used herein refers to a material having elastomeric or rubbery properties. Elastomeric materials, such as thermoplastic elastomers, are generally capable of recovering their shape after deformation when the deforming force is removed. Specifically, as used herein, elastomeric is meant to be that property of any material which upon application of an elongating force, permits that material to be stretched to a length which is at least about 25 percent greater than its relaxed length, and that will cause the material to recover at least 40 percent of its elongation upon release of the stretching elongating force.

"Foam polymer formula" as used herein includes the foamable polymers, and may include one or more of the following: nucleating agent, plasticizing agent, surfactant, bioactive agent, dyes, contrast agents, and any other additives. This formula is heated and mixed to create a polymer melt.

"Molecular weight" as used herein, unless otherwise specified, refers to the weight average molecular weight (Mw), not the number average molecular weight (Mn), and is measured by GPC relative to polystyrene.

"Nucleant" as used herein refers to a compound which when incorporated in certain plastics form nuclei for growth of crystals in the polymer melt.

"Open cell" as used herein means a cell where the membrane surrounding the cavity is partly missing, or has at least one hole that connects the cell to an adjacent cell, such that fluid can move between the adjacent cells. The percentage of open cells may be determined using a gas pycnometer either by the method of ASTM D6226-10 (Standard test method for open cell content of rigid cellular plastics) or ISO 4590:2002 (Rigid cellular plastics—Determination of the volume percentage of open cells and of closed cells).

"Plasticizer" refers to a chemical agent that can be added to a polymer to make it more flexible. Adding a plasticizing agent to a polymer typically lowers the glass transition temperature of the plasticized polymer.

"Copolymers of poly-4-hydroxybutyrate" as generally used herein means any polymer containing 4-hydroxybutyrate with one or more different hydroxy acid units.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, Mass.).

"Polymer" as used herein generally includes but is not limited to, homopolymers, copolymers, including block, grail, random and alternating copolymers, terpolymers, etc., and blends and modifications thereof. Furthermore, unless otherwise specifically limited, the term "polymer" shall include all possible molecular geometrical configurations of the material. These configurations include, but are not limited to isotactic, syndiotactic and atactic symmetries.

"Surfactant" is a compound, such as a detergent or wetting agent, which affects the surface tension of fluids.

I. Composition

Methods have been developed to produce substantially closed cell foams of P4HB and copolymers thereof with densities less than 0.75 g/cm$^3$, and more preferably less than 0.5 g/cm$^3$. These methods may be used to produce closed cell foams that have an open cell content of less than 50%, and more preferably less than 20%. The cells typically have a maximum diameter of less than 5 mm. The methods may be run continuously, which is particularly advantageous in manufacturing. The substantially closed cell foams are prepared by melt-foaming.

A. Polymers

The processes described herein can typically be used with compositions including poly-4-hydroxybutyrate (P4HB) or a copolymer thereof. Copolymers include 4-hydroxybutyrate with another hydroxyacid, such as 3-hydroxybutyrate, and 4-hydroxybutyrate with glycolic acid or lactic acid monomer. P4HB and copolymers thereof can be obtained from Tepha, Inc. of Lexington, Mass.

In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 1000 kDa and even more preferably between 100 kDa to 600 kDa. A weight average molecular weight of the polymer of 50 kDa or higher is preferred. The molecular weights of the P4HB homopolymer and copolymers may be varied in order to control the melt viscosity of the foamable melt.

If desired, the P4HB homopolymer or copolymers may be blended or mixed with other materials prior to melt-foaming. In a particularly preferred embodiment, P4HB and its copolymers may be blended with other absorbable polymers. Examples of other absorbable polymers include, but are not limited to, polymers including glycolic acid, lactic acid, 1,4-dioxanone, trimethylene carbonate, 3-hydroxybutyric acid, caprolactone, including polyglycolic acid, polylactic acid, polydioxanone, polycaprolactone, copolymers of glycolic and lactic acids such as VICRYL® polymer, and the MAXON® and MONOCRYL® polymers. Other absorbable polymers that may be blended with P4HB homopolymer or copolymers thereof include, but are not limited to, poly (orthoesters); polyanhydrides; poly(phosphazenes); polyhydroxyalkanoates; synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly(amino acids)); polyesteramides; poly (alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone or combinations thereof. The ratio of the P4HB homopolymer or copolymer thereof in the blend to the other polymer component(s) may be varied in order to select the desired properties of the substantially closed cell foams.

The P4HB homopolymer and copolymers thereof may also be blended with non-degradable polymers, including thermoplastic polymers. Suitable polymers include styrene polymers, such as polystyrene and copolymers thereof; polyolefins, such as polyethylene, polypropylene, polybutylene; polyesters, such as polyalkylene terephthalate; polyalkylene oxides, such as polyethylene oxide and polypropylene oxide; polyvinyl acids; polyacrylates, including polymethylmethacrylate; polycarbonates; polyacrylamides; polyvinyl alcohol; polyvinyl ethers; polyvinyl pyridine; polyurethanes; starch-based polymers; cellulose-based polymers; polyetherimides; polyphosphazene; and polyamides.

Compatibilizers may be included in blends of P4HB and copolymers thereof with other polymers in order to improve foamability and mechanical properties. The blends may also be crosslinked, for example, using free radicals and chemical crosslinking agents. Suitable crosslinking agents include, but are not limited to: gamma irradiation, ultraviolet light, gas plasma, and bifunctional crosslinking agents reactive toward hydroxyl and/or carboxylic acid groups, such as carbodiimide and diisocyanates. In certain embodiments, the covalent crosslinking agent is selected from epichlorohydrin, gluteraldehyde, hexamethylene diisocyanate, adipic acid hydrazide, and 1-ethyl-3-(3-dimethylaminopropyl)carbodiimide hydrochloride.

B. Substantially Closed Cell Foams

It has been discovered that substantially closed cell foams including P4HB and copolymers thereof can be prepared by melt-foaming. These foams have densities of less than 0.75 g/cm$^3$, and more preferably less than 0.5 g/cm$^3$. In a preferred embodiment, substantially closed cell foams including P4HB and copolymers thereof can be prepared by melt-foaming with an open cell content of less than 50%, and more preferably less than 20%. In contrast, foams including P4HB and copolymers thereof produced by particulate leaching as disclosed by WO 05/020825 to Terenghi et al. have open cell structures such that fluid can move between adjacent cells. Foams including P4HB and copolymers thereof produced by thermal phase separation, and previously disclosed by WO 00/56376 to Williams et al., have open cell structures.

The production of substantially closed cell foams including P4HB and copolymers thereof is a major advantage in certain medical applications, for example, where the following properties are desirable: higher strength, ability to restrict the movement of bodily fluids, capacity to protect a wound from infection and provide barrier protection, ability to maintain an optimum environment for wound healing by controlling wound moisture content, and the capacity to protect a wound from impact or to apply pressure on a wound. Accordingly, substantially closed cell foams including P4HB and copolymers thereof can be used, for example, in both soft and hard tissue repair, to heal wounds, control bleeding, protect wound beds, prevent infection, apply pressure to a tissue surface or structure, prevent movement of bodily fluids, absorb fluids, deliver bioactive agents, reinforce tissue structures, separate tissues, and regenerate tissues.

The substantially closed cell foams with an open cell content of less than 50%, and a density of less than 0.75 g/cm$^3$ can be prepared by appropriate choice of (i) melt properties, including selection of polymer molecular weight, heating and cooling rates, and control of melt viscosity, (ii) blowing agent, (iii) concentration of blowing agent, (iv) foam polymer formula, including the use of polymer blends, nucleants, plasticizers, surfactants, and blowing agent activators, if any, (v) pressure differential, and (vi) equipment set up.

It has been discovered that a particular advantage of using P4HB and copolymers thereof to prepare closed cell foams is the relatively high ductility of these polymers that allows the cell walls to yield, and the cells to grow without collapse. Cells with maximum sizes of up to 5 mm can be prepared without cell collapse.

In a preferred embodiment, substantially closed cell foams are prepared from foam polymer formulas including P4HB and copolymers thereof (in pellet form) with weight average molecular weights of 100 kDa to 600 kDa, and moisture contents of less than 0.03% by weight, using a tandem screw-type extruder. The temperatures for the heat zones (usually 4) to melt the foam polymer formula are set between 150 and 220° C. (and no higher than 260° C.), and the extruder speed is set at 20-400 rpm, and more preferably 20-100 rpm. In a preferred embodiment, pellets of the foam polymer formula are hopper fed into the extruder, and the screw conveys the polymer formula down the barrel. During passage down the extruder barrel, the polymer composition melts, the blowing agent is introduced, and the composition and blowing agent are mixed to form a foamable melt.

In a preferred embodiment, the blowing agent is added to the foam polymer formulas including P4HB and copolymers thereof in an amount between about and about 10% by weight. Examples of blowing agents that can be used to create the foams including poly-4-hydroxybutyrate homopolymer and copolymers thereof include compounds that decompose at extrusion temperatures to release large volumes of gas, volatile liquids such as refrigerants, hydrocarbons, and ambient gases or combinations thereof. Suitable blowing agents include nitrogen, carbon dioxide, air, argon, helium, methane, ethane, propane, butanes, hexanes, and halogenated hydrocarbons. Preferred blowing agents have low toxicity, appropriate volatility, adequate solubility in the molten foam polymer formula at the concentration required for the necessary degree of foaming, low reactivity (including at elevated temperatures), acceptable diffusion rates, relatively low molecular weights, and must provide the polymer melt (solution) pressure necessary to expand and form foams. Particularly preferred blowing agents are carbon dioxide and nitrogen.

After mixing of the blowing agent, the polymer melt is cooled in the second extruder to a temperature that will prevent collapse of the cells upon discharge, and the foamable melt is extruded through a die to a lower pressure, preferably atmospheric pressure, resulting in Wining and cooling of the polymer composition. The foams may also be produced using a single extruder instead of a tandem extruder with a cooling zone located prior to discharge of the foamable melt.

It has also been discovered that substantially closed cell foams including P4HB and copolymers thereof can be prepared by melt-foaming with unexpectedly high retention of polymer weight average molecular weight. Notably, the weight average molecular weight of the P4HB homopolymer and copolymers decrease less than 50% during melt-foaming, and more preferably less than 25%. Retention of molecular weight during processing is important when high initial strength is required, and also when prolonged strength retention is required in in vivo (for example, in reinforcement of tissue structures).

C. Foam Polymer Formulas

If desired, nucleating agents, plasticizers, surfactants, foaming aids, dyes, compatibilizers, emulsifiers, bioactive agents, ceramics, contrast agents, radiopaque markers, radioactive substances, and other additives may also be added to the foam polymer formulas including P4HB and copolymers thereof. Alternatively, bioactive agents, ceramics, contrast agents, radiopaque markers, and radioactive substances can be added directly to the foam.

In an embodiment, nucleating agents can be added to the foam polymer formulas in order to improve the gas bubble formation during foaming, and enhance the properties of the foams including P4HB and copolymers thereof. The amount of nucleating agent needed to improve the gas bubble formation and enhance the foam properties will vary according to the nature of the nucleating agent, the foam properties desired, as well as the polymer composition, pressure, and foaming temperature. Generally, the cell density and open cell content of the foams including P4HB and copolymers thereof will increase with increasing nucleating agent concentration. In a preferred embodiment, the concentration of nucleating agent will typically range from 0.1 to about 5% by weight of the foam polymer formula. Suitable nucleating agents include amino acids disclosed by U.S. Pat. No. 5,516,565 to Matsumoto; oligomers of PHA polymers, including P4HB oligomers and copolymers thereof; talc; boron nitride; calcium and magnesium carbonate; silica; blends of citric acid and sodium carbonate, and coated particles thereof; barium and calcium stearate; and other compounds that facilitate the formation of crystals in the polymer melt.

Plasticizers may also be incorporated in the foam polymer formulas for melt-foaming to enhance the properties of the foams including P4HB and copolymers thereof. The amount of plasticizer added needs to be carefully controlled because the plasticizer can thin the cell membranes, increase the open cell content of the foams by creating pores in the cell membranes, and cause cellular collapse if the plasticizer concentration is too high. (It should be noted that it is possible to adjust the polymer melt index to partially or fully offset the plasticizing agent's effects, or as described further below, a surfactant can be incorporated into the foam polymer formula for this purpose.) The concentration of plasticizer needed will depend upon the effectiveness of the plasticizer, and its ability to increase the chain mobility of the composition including P4HB and copolymers thereof. The concentration of plasticizer needed can often be gauged from the plasticizer's ability to depress the glass transition temperature of the polymer composition including P4HB and copolymers thereof. In an embodiment, the concentration of the plasticizing agent is between 0.5% and 20% by weight of the foam polymer formula, and more preferably between 1% and 10% by weight of the foam polymer formula. Suitable plasticizing agents include those disclosed by U.S. Pat. No. 6,905,987 to Noda et al.; petroleum-based oils; palm oil; citrates; stearates; phthalates; waxes; polyols; esters of alcohols and organic acids, including fatty acids and esters; and combinations thereof. Particularly preferred plasticizing agents include acetyl tributyl citrate; acetyl triethyl citrate; p-test-butylphenyl salicylate; butyl stearate; butylphthalyl butyl glycolate; dibutyl sebacate; di-(2-ethylhexyl) phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triacetin (glycerol triacetate) triethyl citrate; polymers and copolymers of propylene and ethylene glycols; and polymers of tetrahydrofuran.

In another embodiment, a surfactant may be included in the foam polymer formula including P4HB and copolymers thereof to help stabilize the cells and prevent cellular collapse. This is particularly desirable if the foam polymer formula also comprises a plasticizer as the surfactant can mediate the impact of the plasticizer on the melt viscosity, help promote bubble formation, control the open cell content of the foam, and help create cell size uniformity. The use of a surfactant is especially helpful when it is desirable to make foams including P4HB and copolymers thereof with low densities, particularly when plasticizing agents are present. By decreasing surface tension, the surfactant reduces the pressure differential required to maintain a given bubble size, decreases pressure differences between bubbles of different sizes, and increases the bubble nucleation rate. The inclusion of a surfactant in the foam polymer formula can also increase the wettability of the resulting foam, which can be advantageous in certain applications, for example, where it is desirable to absorb fluid, maintain a moist environment, or enhance attachment of human and animal cells to the foam. In an embodiment, the concentration of surfactant in the foam polymer formula including P4HB and copolymers thereof will range from 1 to 20% by weight, and more preferably from 2 to 10% by weight. Surfactants that can be included in the foam polymer formula include cationic, anionic, amphoteric, and nonionic surfactants, including amino acid based surfactants and glycerolipid surfactants, and combinations thereof. Particularly preferred surfactants include polyethylene sorbitol esters, including TWEEN® 20 and TWEEN® 80, polyethylene glycol (PEG) based surfactants, and copolymers of ethylene and propylene glycol, such as PLURONIC® surfactants.

In a further embodiment, the foam polymer formula may include other foaming aids in addition to surfactants. Examples include stearic acid, salicylic acid, fatty acids, and metal oxides.

In an embodiment, the foam polymer formula includes a dye. Particularly preferred dyes include D&C Violet No. 2, D&C Green No. 6, and other dyes listed in the Code of Federal Regulations: Part 73 Subpart for drugs, Part 74 Subpart B for drugs, Part 73 Subpart C for cosmetics, Part 74 Subpart C for cosmetics, Part 73 Subpart D for medical devices, and Part 74 Subpart D for medical devices. In a preferred embodiment, dye is added to the foam polymer formula so that the concentration of dye in the substantially closed cell foam is 0.5% by weight or less, and more preferably 0.3% by weight or less.

In another embodiment, the foam polymer formula includes a ceramic, preferably a resorbable ceramic. Ceramics that can be used must be biocompatible. In a particularly preferred embodiment, the body is able to resorb the ceramic if the foam is implanted. Examples of resorbable ceramics include tricalcium phosphate (α and β forms of TCP—with a nominal composition of $Ca_3(PO_4)_2$), biphasic calcium phosphate (BCP), calcium sulfate, hydroxylapatite, calcium carbonate, and other calcium phosphate salt-based bioceramics. Bioactive glasses may also be incorporated into the foam polymer formula. Bioactive glasses are composed of $SiO_2$, $Na_2O$, $CaO$ and $P_2O_5$ in specific proportions.

In yet another embodiment, the foam polymer formula includes a thermoplastic elastomer, in addition to P4HB and copolymers thereof, to improve the softness, flexibility, elasticity and resiliency of the substantially closed cell foams.

In still yet another embodiment, the foam polymer formula includes emulsifiers and compatibilizers.

D. Structures and Devices Including Foams

The structures include at least the aforementioned substantially closed cell extruded foams including P4HB and copolymers thereof, but a structure may also include a foam that has subsequently been shaped by molding, stamping, calendaring, or cutting. These processes can be used to convert a two-dimensional closed cell foam into a three-dimensional closed cell foam.

In a particularly preferred embodiment, the extruded foams may be further processed by thermoforming. The latter is a particularly preferred processing technique because the foams retain their shapes after being molded. Extruded foams including P4HB and copolymers thereof may be heated to a pliable forming temperature, and molded into a specific form. In a particularly preferred embodiment, the heated pliable foams may be stretched either over or into a preformed mold using a vacuum, and allowed to cool to the desired finished shape.

In another preferred embodiment, an extruded foam including P4HB and copolymers thereof may be further processed by compression molding. In a preferred method, a foam including P4HB and copolymers thereof is shaped by placing the foam in a temperature controlled mold, heating the foam until it is at a pliable forming temperature, and then shaping the foam by applying pressure using a hydraulic press.

The extruded foams including P4HB and copolymers thereof may be used alone or in combination with other structural components. For example, the foams may be combined or laminated with a nonwoven fabric, woven fabric, knitted mesh, fiber, or film. These composite structures may be formed, for example, using compression molding or thermoforming. The extruded foams may also be combined or laminated with other foam structures.

In addition to processing the extruded foams including P4HB and copolymers thereof by molding, stamping, calendaring or cutting, the foams may be further processed using heat treatments, chemical treatments, surface treatments, and or gas plasma treatments.

The substantially closed cell foams including P4HB and copolymers thereof have properties that are substantially improved for many medical applications relative to glycolic and lactic acid derived melt-foamed structures. While structures derived from polymers of glycolic and lactic acids release acidic monomers, the substantially closed cell foam structures derived from P4HB and copolymers thereof release much less acidic degradation products since the 4-hydroxybutyric acid monomer is less acidic (i.e. has a higher pKa) than that of glycolic and lactic acids. The closed cell foam structures derived from P4HB and copolymers thereof will also retain strength longer in vivo due to the slower degradation of these polymers in vivo, and therefore the structures will retain their integrity for longer. This is important where healing requires a prolonged period.

The substantially closed cell foams may be used to prepare structures that are suitable for use as medical devices. In particular, structures can be formed for use as implantable medical devices and in wound healing. For example, the substantially closed cell foam structures including P4HB and copolymers thereof may be used to make partially or fully absorbable biocompatible medical devices, or components thereof. Such devices include, but are not limited to: devices for use in both soft and hard tissue repair, to heal wounds, control bleeding, protect wound beds, prevent infection, apply pressure to a tissue surface or structure, prevent movement of bodily fluids, absorb fluids, deliver bioactive agents, reinforce tissue structures, separate tissues, prevent adhesions, and regenerate tissues, and including wound dressings, tapes, patches, seals, scaffolds, hemostats, pledgets, wound closure devices, vascular closure devices, repair patches, bulking and filling agents, retention membranes (for example, to retain bone graft), surgical foams, compression bandages, orthopedic foams, surgical foams, orthodontic devices, and drug delivery devices. The substantially closed cell foams may also be used as tissue engineering scaffolds, hernia repair devices, cardiovascular patches, foams for cosmetic surgery, including face lift, neck lift, eyebrow lift, and breast lift, foams for breast reconstruction, slings, rotator cuff repair devices, meniscus repair devices, guided tissue repair/regeneration devices, articular cartilage repair devices, osteochondral repair devices, bone void fillers, nerve guides, tendon repair devices, intracardiac septal defect repair devices, including but not limited to atrial septal defect repair devices and patent foramen ovale (PFO) closure devices, left atrial appendage (LAA) closure devices, pericardial patches, vein valves, heart valves, bone marrow scaffolds, meniscus regeneration devices, ligament and tendon grafts, spinal fusion devices, skin substitutes, dural substitutes, and bone graft substitutes.

E. Bioactive Agents and Other Additives

The structures and devices may comprise other components, including one or more bioactive agents. These other components may either be incorporated at the time of melt-foaming or after the melt-foaming process. It includes without limitation physiologically or pharmacologically active substances that act locally or systemically in the body. Bioactive agents include biologically, physiologically, or pharmacologically active substances that act locally or systemically in the human or animal body. Examples can include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, growth factors, fibronectin, laminin, vitronectin, integrins, antibiotics, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, lipoproteins, hyaluronic acid and derivatives thereof, allograft material, xenograft material, ceramics, nucleic acid molecules, antisense molecules, aptamers, siRNA, nucleic acids, and combinations thereof.

The structures and devices may also be seeded with cells to improve tissue ingrowth and healing. In another embodiment, the structures and devices comprise signaling ligands, including members of the TGF-beta family, bone morphogenic proteins, fibroblast growth factors-1 and -2, platelet-derived growth factor-AA and -BB, and platelet rich plasma and vascular endothelial cell-derived growth factor. In yet another preferred embodiment, the structures and devices may be used for the controlled release of drugs, or incorporate systems for the controlled release of drugs. In still another embodiment, the structures and devices may be coated with agents that increase their wettability, and the attachment of biological cells to the foams.

II. Methods of Manufacturing Melt-Blown Closed Cell Foams of P4HB and Copolymers Thereof, and Products Derived Therefrom A. Method of Making Substantially Closed Cell Foams of P4HB Polymer or Copolymer In a preferred method, substantially closed cell foams including P4HB polymer or copolymer thereof may be prepared using a tandem screw-type extruder. This set up preferably comprises one extruder set up with several zones that include: feed and conveying, compression, melting, metering and mixing zones with an inlet for a physical blowing agent normally located between the metering and mixing zones. A second extruder is connected downstream of the first extruder via a heated crossover supply pipe in a normal tandem setup, and used to cool the melt prior to discharge. In a less preferable equipment setup, a single extruder can be used typically with a cooling zone located prior to discharge, foaming, and shaping.

In a preferred embodiment, the first extruder (or single extruder) is hopper loaded with a composition including poly-4-hydroxybutyrate or copolymer thereof and any desired additives using metering equipment, or the additives maybe added to the polymer separately, for example, in a masterbatch containing an additive concentrate in the polymer. In a particularly preferred embodiment, the foam polymer formula is added in pelletized form. The polymer and any additives are subsequently heated in the extruder to form the melt system. This stage of the process is preferably accomplished using several heating zones with heating of the polymer to a temperature above its melt temperature to form a polymer melt. In a preferred embodiment, the heating zones are set to temperatures ranging from 150 to 260° C. The blowing agent is then introduced, and the agent and polymer melt are thoroughly mixed. In the tandem extruder configuration, the resulting foamable melt is cooled in the second extruder to a temperature that will prevent collapse of the cells upon discharge. In a particularly preferred embodiment, the temperature of the foamable melt is tightly controlled using, for example, process temperature control loops, to produce the desired bubble nucleation within the melt system. After cooling of the foamable melt to the desired temperature, the melt is extruded through a die to a lower pressure, preferably atmospheric pressure, resulting in foaming and cooling of the polymer. The extrusion die is selected according to the desired shape, dimensions, orientation, and any requirements for foam expansion and cooling of the foam. For example, the equipment can be configured to produce extruded sheet, stranded foam, rod, pipe, block, film, and beads, as well as foam laminates and composites. Suitable dies include slit, circular, and annular dies, and if desired, stretching equipment may be used downstream of the foam discharge.

Blowing agents that can be used to create the foams including poly-4-hydroxybutyrate homopolymer and copolymer can be compounds that decompose at extrusion temperatures to release large volumes of gas, volatile liquids such as refrigerants, hydrocarbons, and ambient gases or combinations thereof. Suitable blowing agents include nitrogen, carbon dioxide, air, argon, helium, methane, ethane, propane, butanes, hexanes, and halogenated hydrocarbons. Preferred blowing agents have low toxicity, appropriate volatility, adequate solubility in the molten polymer at the concentration required for the necessary degree of foaming, low reactivity (including at elevated temperatures), acceptable diffusion rates, relatively low molecular weights, and must provide the polymer melt (solution) pressure necessary to expand and foam the foam polymer formulas including poly-4-hydroxybutyrate and copolymers thereof. Particularly preferred blowing agents are carbon dioxide and nitrogen. The blowing agent can be added to the compositions including P4HB and copolymers thereof in an amount between about 1% and about 10% by weight.

If desired, nucleants, plasticizers, and blowing agent activators may be used in the foaming process to control cell density, cell structure, and foam properties. The actual amount of these agents will vary according to the desired foam structure, as well as the processing conditions. Small quantities of immiscible polymers may also be added in order to disrupt the cell wall, and provide foams with an increased level of open cells.

In an embodiment, secondary post-treatment processes may be used to further modify the properties of the foams including poly-4-hydroxybutyrate homopolymer and copolymers. These processes include needling, stretching, brushing, scarfing, buffing/sanding, calendaring, thermoforming, perforating, post-densification, and lamination. In the latter case, the same or different foams and materials may be laminated together.

B. Method of Making Structures and Devices of Substantially Closed Cell Foams of P4HB Polymer or Copolymer Thereof.

A particular advantage of the melt-foaming method described herein is that the substantially closed cell foams may be produced in different shapes and forms that can subsequently be processed by methods such as molding, forming, stamping, calendaring, embossing, or cutting, including cutting with lasers, scissors, and knives.

In an embodiment, sheets of substantially closed cell foams including P4HB and copolymers thereof are produced by melt-foaming, and are subsequently processed by compression molding.

In a particularly preferred method, sheets of substantially closed cell foams including P4HB and copolymers thereof are produced by melt-foaming, and are subsequently processed by thermoforming. The sheet foams are heated until they soften, and then molded or stamped using a thermoformer into the desired devices and structures.

The present invention will be further understood by reference to the following non-limiting example.

Example 1

Preparation of a Substantially Closed Cell Foam Including P4HB and PLLA by Melt-Foaming An extrusion line consisting of a 27 mm, 40/1 L/D co-rotating fully intermeshing twin screw extruder, conveyor belt, and cooling fans was used to produce a number of foam structures, with and without nucleating agent (0 to 2.0 wt %), using 1.5, 2 and 4 mm diameter dies and the following method: Using a gravimetric feeder or multiple gravimetric feeders, P4HB (Tepha, Inc., Lexington, Mass.) and PLLA (poly-1-lactic acid, with a D-isomer content of >5%) were blended at a ratio of 50/50 wt %, and fed into the main feed hopper of the extruder at a total rate of 5-7 lbs/hr (2.27-3.18 kg/hr). The P4HB had a starting weight average molecular weight of 418 kDa, the PLLA had a starting weight average molecular weight of 258 kDa, and both polymers were dried to moisture contents of less than 150 ppm prior to processing. Calcium carbonate and talc were used separately as nucleants at levels of 0.5 wt % and 2.0 wt %, respectively, when nucleants were used. The polymer blend was fed to the extruder at a screw speed ranging from 25-50 rpm, and allowed to plasticize. Supercritical $CO_2$ gas was injected in the extruder barrel at the end of the transition zone, at a pressure of 3000-3600 psi (20.68-24.82 MPa), and the $CO_2$ in the liquid phase was mixed with molten polymer in the extruder to distribute the $CO_2$ uniformly in the polymer matrix. A reverse temperature profile was used to allow the polymer melt including the $CO_2$ to cool, prior to discharging the material from the extruder through the die. The foamable melt discharged from the extruder at a pressure ranging from about 1000-2400 psi (6.89-16.55 MPa). Substantially closed cell foamed structures were created when the solubilized gas expanded as it was discharged from the extruder. The outer layer of the extrudate was quenched using forced air, completely entrapping the gas bubbles in the polymer, and forming and maintaining a substantially closed cell foam structure. The extruded foam was cooled further using fans as it continued along the conveyor belt until the foam was completely cooled. The measured weight average molecular weight of the P4HB/PLLA blended foam without using a nucleating agent was 347 kDa. The average densities of representative foams are shown in Table 1.

TABLE 1

| Composition of Sample | Average Density g/cm$^3$ |
|---|---|
| 50/50 wt % P4HB/PLA, no nucleant | 0.186 |
| 50/50 wt % P4HB/PLA, talc as nucleant | 0.156 |

Modifications and variations of the methods and compositions will be apparent from the foregoing detailed description and are intended to come within the scope of the appended claims.

We claim:

1. A foam composition comprising poly-4-hydroxybutyrate (P4HB) homopolymer, wherein the foam comprises closed cells as measured by ASTM D6226-10, and wherein the foam has an open cell content of less than 50%, and wherein the P4HB homopolymer is not crosslinked.

2. The composition of claim 1 wherein the foam has a density of less than 0.75 g/cm$^3$.

3. The composition of claim 1 wherein the cells of the foam have a maximum diameter of less than 5 mm.

4. The composition of claim 1 wherein the weight average molecular weight of the poly-4-hydroxybutyrate homopolymer decreases less than 25% during the processing of the polymer into a cell foam comprising closed cells.

5. The composition of claim 1 further comprising one or more of the following: nucleating agent, plasticizing agent, surfactant, thermoplastic elastomer, foaming aid, dye, bioactive agent, contrast agent, radiopaque agent, radioactive marker, radioactive substance, resorbable polymer, and non-degradable polymer.

6. The composition of claim 5 wherein the foam comprises one or more of the following: 0.1-5% by weight of the nucleating agent, 0.5-20% by weight of the plasticizing agent, 1-20% by weight of the surfactant, and up to 0.5% by weight of the dye.

7. The composition of claim 5 wherein the foam comprises one or more resorbable polymers comprising poly (lactide); poly(glycolide); poly(lactide-co-glycolide); poly (lactic acid); poly(glycolic acid); poly(lactic acid-co-glycolic acid); polycaprolactone; poly(orthoester); polyanhydride; poly(phosphazene); polyhydroxyalkanoates; poly-3-hydroxybutyrate; poly-3-hydroxybutyrate-co-3-hydroxyvalerate; synthetically or biologically prepared polyester; polyester with one or more of the following monomeric units: glycolic, lactic; trimethylene carbonate, p-dioxanone, or e-caprolactone; poly(lactide-co-caprolactone); polycarbonate; tyrosine polycarbonate; polyamide; synthetic or natural polyamide, polypeptide, poly(amino acid); polyesteramide; poly(dioxanone); poly(alkylene alkylate); polyether; polyethylene glycol; polyethylene oxide; polyvinyl pyrrolidone; polyurethane; polyetherester; polyacetal; polycyanoacrylate; poly(oxyethylene)/poly(oxypropylene) copolymer; polyacetal, polyketal; polyphosphate; phosphorous-containing polymer; polyphosphoester; polyalkylene oxalate; polyalkylene succinate; poly(maleic acid); chitin; chitosan; modified chitosan; hyaluronic acid and derivatives thereof; hydrophilic or water soluble polymer.

8. The composition of claim 1 wherein the closed cells contain a blowing agent.

9. The composition of claim 8 wherein the blowing agent is one or more of the following: nitrogen, carbon dioxide, air, argon, helium, methane, ethane, propane, butanes, hexanes, and a halogenated hydrocarbon.

10. A composition according to claim 1 wherein the poly-4-hydroxybutyrate homopolymer has a weight average molecular weight greater than 50 kDa relative to polystyrene.

11. A method for preparing the composition of claim 1 by using melt-foaming wherein the method comprises the following steps: (i) preparing a foam polymer formula comprising poly-4-hydroxybutyrate homopolymer, (ii) heating the foam polymer formula to create a polymer melt in an extruder, (iii) introducing a blowing agent to the polymer melt, and (iv) cooling and extruding the foamable melt to form a substantially closed cell foam.

12. The method of claim 11 wherein (i) the moisture content of the foam polymer formula is less than 0.03% by weight, (ii) a temperature of 150-260° C. is used to melt the foam polymer formula, and (iii) the amount of blowing agent introduced to the polymer melt is 1-10% by weight.

13. The foam of claim 1, wherein the foam is made from a P4HB homopolymer by a polymer foaming process, wherein the process does not include a crosslinking agent.

* * * * *

UNITED STATES PATENT AND TRADEMARK OFFICE
CERTIFICATE OF CORRECTION

PATENT NO. : 10,689,498 B2
APPLICATION NO. : 14/464099
DATED : June 23, 2020
INVENTOR(S) : Dennis Connelly et al.

Page 1 of 1

It is certified that error appears in the above-identified patent and that said Letters Patent is hereby corrected as shown below:

In the Specification

Column 6, Line 66, replace "polycaprolcatone" with --polycaprolactone--.
Column 8, Line 29, replace "between about and about 10%" with --between about 1% and about 10%--.
Column 8, Line 52, replace "resulting in Wining and" with --resulting in foaming and--.
Column 9, Line 61, replace "p-test-butylphenyl salicylate" with --p-tert-butylphenyl salicylate--.

In the Claims

Claim 1, Column 15, Line 35, replace "and wherein" with --wherein--.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*